(12) United States Patent
Di Bugno et al.

(10) Patent No.: US 6,921,841 B2
(45) Date of Patent: Jul. 26, 2005

(54) PROCESS FOR THE SYNTHESIS OF OPTICALLY ACTIVE ANTHRACYCLINES

(75) Inventors: Cristina Di Bugno, Pisa (IT); Fabio D'Arata, Cascina (IT); Alessio Ramacciotti, Leghorn (IT); Paolo Crotti, Capannori (IT)

(73) Assignee: Menarini Richerche S.p.A., Pomezio (IT)

( * ) Notice: Subject to any disclaimer, the term of this patent is extended or adjusted under 35 U.S.C. 154(b) by 0 days.

(21) Appl. No.: 10/416,649

(22) PCT Filed: Nov. 15, 2001

(86) PCT No.: PCT/EP01/13217

§ 371 (c)(1),
(2), (4) Date: May 14, 2003

(87) PCT Pub. No.: WO02/40496

PCT Pub. Date: May 23, 2002

(65) Prior Publication Data

US 2004/0029819 A1 Feb. 12, 2004

(30) Foreign Application Priority Data

Nov. 16, 2000 (IT) ............................ FI00A0237

(51) Int. Cl.$^7$ .................. C07C 45/00; C07C 49/213; C07H 1/00
(52) U.S. Cl. .................. 568/309; 568/308; 536/6.4; 536/18.5
(58) Field of Search ................ 568/308, 309; 536/6.4, 18.5

(56) References Cited

U.S. PATENT DOCUMENTS 4,077,988 A   3/1978  Arcamone ............... 260/376
4,405,713 A * 9/1983  Fujiwara et al. ............ 435/78

OTHER PUBLICATIONS

XP002188353, Rao, A.V. Rama et al., "A Stereoconvergent Synthesis of (=)–4–Demethoxydaunomycin," J. Chem. Soc., Chem. Commun. 1984, (7), pp. 453–455.

XP001058968, Rho, Young S. et al., "Total Synthesis of a New 7–Deoxyidarubicinone Derivative through the Functionalization of an A–Ring Side Chain," Bull. Korean Chem. Soc. (2000), vol. 21, No. 8, pp. 774–778.

XP002188593, Tanno, Norihiko et al., "Preparation of dihydroxytetrahyrdronaphthacenedione derivatives as intermediates for anthracycline antibiotics," Sumitomo Pharmaceuticals Co., Ltd., Japan, Jun. 16, 1987.

XP002188355, Nakajima, M. et al., "Short–Step Asymmetric Synthesis of Anthracycline Antibiotics via Enantioselective Dihydroxylation by Osmium Tetroxide with Chiral Diamine," Tetrahedron, vol. 49, No. 47, 1993, pp. 10807–10816.

XP008000090, Rao, A. V. Rama et al., "Total Synthesis of (.=–.)–4–Demethoxydaunomycinone," Indian J. Chem., Sect. B (1985), 24B(7), pp. 697–702.

XP002188354, Arcamone, F. et al., "Synthesis and antitumour activity of new daunorubicin and adriamycin analogues," Experientia, vol. 34 No. 10, 1978, pp. 1255–1257.

XP002188356, Russell, R. A. et al., "An Economical and Versatile Synthesis of 5,8–Dialkoxy–2–acetyl–3,4–dihydronaphthalenes: Key Precursors for the Synthesis of Chiral Anthracyclines," J. Chem. Soc, Chem. Commun., 1983, pp. 994–995.

* cited by examiner

*Primary Examiner*—Elli Peselev
(74) *Attorney, Agent, or Firm*—Lorusso & Loud; Jeffrey D. Washville; Marc A. Vivenzio

(57) ABSTRACT

It is described a process for the synthesis of optically active anthracyclines by the fact that the key intermediate (R)2-acetyl-2-hydroxy-1,2,3,4-tetrahydronaphtalene 5,8-dialkoxy-3,4-dihydronaphtalene by acylation asymmetric dihydroxylation, transformation into chloroacetate, dehydrochloridation and final hydrolysis.

10 Claims, No Drawings

PROCESS FOR THE SYNTHESIS OF OPTICALLY ACTIVE ANTHRACYCLINES

This application is 371 of PCT/EP01/13217 filed Nov. 15, 2001.

FIELD OF THE INVENTION

The present invention refers to a process for the synthesis of optically active anthracyclines wherein the optically active key intermediate (R) 2-acetyl-2-ihydroxy-1,2,3,4-tetrahydronaphthalene 5,8-dialkoxy of formula I.

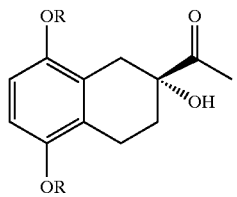

wherein: $R=C_{1-3}$ alkyl, preferably methyl. is prepared starting from 5,8-dialkoxy-3,4-dihydronaphthalene by acylation, asymmetric dihydroxylation, transformation into chloroacetate dehydrochloridation and final hydrolysis.

The invention refers also to the intermediates of formula V e VI:

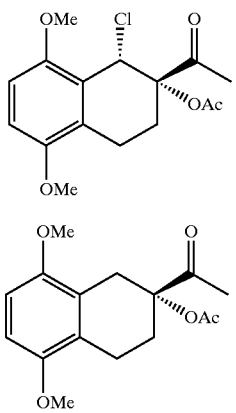

Having an enantiomeric excess higher than 95%.

STATE OF THE ART

As it is known the anthracyclines of formula VIII

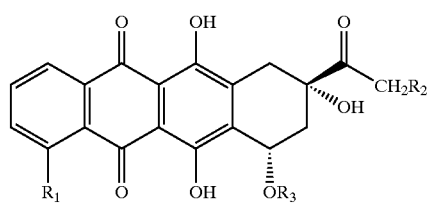

Wherein: $R_1$=H, OH, $OCH_3$; $R_2$=H, OH; $R_3$=X, Y o Z where

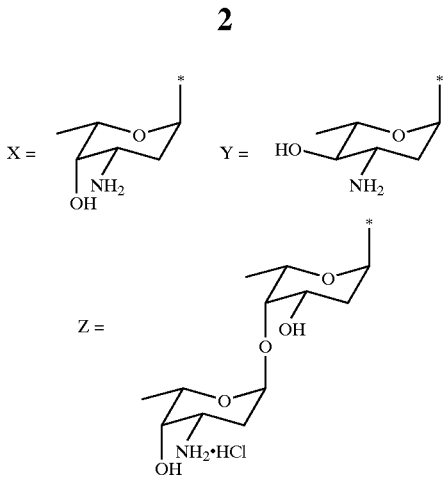

are compounds having a wide therapeutic use as antineoplastic drugs.

Known compounds of formula VIII having the above said properties are for example Daunomicin (VIII, wherein: $R_1$=$OCH_3$, $R_2$=H, $R_3$=X), la Doxorubicin (VIII wherein: $R_1$=$OCH_3$, $R_2$=OH, $R_3$=X), l'Hydrarubicin (VIII wherein: $R_1$=H, $R_2$=H, $R_3$=X) e l'Epirubicin (VIII wherein: $R_1$=$OCH_3$, $R_2$=OH, $R_3$=Y), or the compounds described in EP721456, in particular the compound of formula VIII wherein $R_1$=H, $R_2$=OH, $R_3$=Z, disaccharide anthracycline which is now under clinical development.

The synthesis of anthracycline of formula VIII requires many step and is normally performed starting from an optically active tetraline of formula I which is reacted by a Friedel-Craftsreaction with phthalic anhydride or its derivatives as phthaloyll dichloride or phthaloyll chloride methylester and thereafter cyclised. The so obtained tetracycle is protected in the 13-oxo position with ethylenglycol, is brominated in position 7 and converted into a 7-OH derivative with known methods (sec Arcamone et al., Experientia, 1978, 34, 1255; Wong et al. Can. J. Chem., 1971, 49, 2712; Swenton et at., Tetrahedron, 1984, 40, 4625). After deprotection the anthracyclinone of formula VII (wherein R.sub.2.dbd.H) is used as such or is converted into a 14 acyloxy derivative (compound of formula VII wherein R.sub.2.dbd.O-acyl) according to known procedures. Thereafter the compounds of formula VII are glycosidated with protected mono- or disaccharides as described in literature (see Arcamone et al., Experientia, 1978, 34, 1255; Terashima et al., Bull. Chem. Soc. Jpn, 1986, 59, 423) and in EP 721456, by deprotection the anthracycline of formula VIII are obtained.

In the above described process, or in other similar processes which include as intermediate a tetraline, the key intermediate is the tetraline of formula I itself as above defined.

This AB synthon (Wong et al. Can. J. Chem, 1971, 49, 2712) allows the formation of the corresponding optically active anthracyclinone of formula VII wherein $R_1$=H, OH, $OCH_3$ and $R_2$=H, OH, O-acyl wherein the acyl group is chosen among formyl, acetyl, mono-, di- or trichloroacetyl, preferably acetyl.

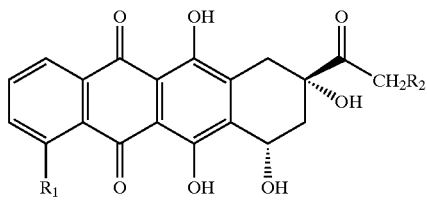

VII

As above said the compound is finally converted in the desired anthracycline.

The stereochemistry of position C-9 of the anthracyclinone is very important for the biological activity of these compounds since only the compounds having (S) configuration in C-9 show an antitumour activity.

Therefore also the tetraline intermediate of formula I must obviously possess the same stereochemistry (i.e. an absolute configuration R).

The tetraline I is normally prepared. According to the literature, as a racemic is mixture starting from 2-acetyl-5,8-dimethoxy tetraline III by oxydrilation in position C-2 with potassium t-butoxide/t-butanole in the presence of oxygen followed by reduction "in situ" (Wong et al., Can. J. Chem., 1971, 49, 2712; Gardner et al., J. Org. Chem. 1968, 33, 3294).

The compound III was prepared, with very low yields by reacting 5,8-dimethoxy-3,4-dihydronaphthalene II with N-N-diphenylacetamide-POCl₃ applying the conditions of the Vilsmeier-Haack reaction followed by the reduction of the double bond.

Several attempts of acylating compound II have been reported but all unsuccessful (Rama Rao et al. Ind. J. Chem. 1985, 24B, 697).

Alternatively the compound III was prepared with a yield of about 50% in 4 steps by reaction of 5,8-diacetoxy-3,4-dihydronaphthalene with acetyl chloride/AlCl₃ and formation of a chloroacetyl derivative, followed by dehydrochloridation with LiCl, hydrolysis and methylation "in situ" (Russell et al. J. Chem. Soc. Chem. Comm. 1983, 994).

Another reaction path for obtaining the precursor III reported in literature includes five steps starting from 5,8-dihydroxy-1,4-diidronphthalene with a total yield of about 50% (Giles et al. S. Afr. J. Chem, 1990, 43, 87).

The racemic tetraline I is thereafter converted into the pure enantiomeric compound using the normal methods applied for the resolution of racemes through diastereolsomeric Schiff bases on the acetyl lateral chain with (−)-1-phenylethylamine (Arcamone et al. BP 02691/75, 1975). Alternatively the enantiomeric pure compound was prepared by Kinetic resolution via a Sharpless asymmetric epoxidation followed by oxidation of the obtained allyl alcohol obtained by reducing 2-acetyl-5,8-dimethoxy-3, 4dihydronaphthalene (Sharpless et al. J. Am. Chem. Soc. 1981, 103, 6237). Another method for obtaining the optically pure tetraline consists in the stereoselective reduction of the racemic mixture with bakers' yeast to diastereolsomeric dioles mixtures followed by chromatographic separation and re-oxidation (Terashima et al., Chem. Pharm. Bull. 1984, 32, 4328).

An asymmetric synthesis of the tetraline I starting from precursor III by enantioselective dihydroxylation is described in M. Nakajima et al. Tetrahedron, 1993, 49, 10807, but the several steps and the final excess of tetraline I and especially the use of osmium tetraoxide in stoichiometric quantities, instead of catalytic, quantities and the use of expensive chiral amines (always in stoichiometric quantities) quantities at a temperature of −110° C., makes very difficult the industrial use of this synthesis.

Other asymmetric synthesis of AB synthon using chiral compounds or compounds comprising chiral derivatives of natural compounds are reported in literature but all these synthesis are very complex and unsuitable for industrial application (Krohn, Angew. Chem. Int. Ed. Engl., 1986, 25, 790).

SUMMARY OF THE INVENTION

The present invention describes a process for the preparation of anthracyclines of formula VIII as above defined VIII wherein the optically active tetraline of formula I as above defined is stereoselectively prepared starting from 5,8-dialkoxy-3,4-dihydronaphthalene II which, contrary to the methods applying the resolution of racemic mixture, which are difficult to perform, and give yields inferior to 30%, shows the advantage of giving the key intermediate I in yields much higher than those reported in literature and is easily industrially exploitable.

In particular, although the literature reported as fruitless, or non interesting because of the low yields, the attempts of acylating compound II (Rama Rao et al. Ind. J. Chem. 1985, 24B, 697, Russell et al. J. Chem. Soc. Chem. Comm. 1983, 994, Giles et al. S. Afr. J. Chem, 1990, 43, 87), the 5,8-dialkoxy-3,4-dihydronaphthalene (compound of formula II wherein R is a group $C_{1-3}$ alkyl, preferably methyl) can surprisingly be acylated in just one step in the presence of an acyl chloride and aluminium trichloride forming the corresponding acyl derivative III. Moreover this innovative application of the procedure of enantioselective catalytic dihydroxylation of olefins (Sharpless et al., Chem. Rev. 1994, 94, 2483) to give the insature acyl derivative allows to obtain the optically active diol IV in a good yield. The compound is thereafter converted into the corresponding 1-chloro-2-acetyl-derivative by Sharpless procedure (Sharpless et al, Tetrahedron, 1992, 48, 10515) and dehalogenated following known methods, for example by catalytic hydrogenation or in the presence of tin and a radical precursor or can be directly dehydroxylated by catalytic reduction. The final hydrolysis of the ester group allows the formation of compound I in good yields and high optical purity.

DETAILED DESCRIPTION OF THE INVENTION

In Schema I it is reported a process for obtaining the tetraline of formula I wherein R=CH₃. In this case the starting product is the 5,8-dimethoxy-3,4-dihydronaphthalene II, obtained by known methods starting from butadiene and p-quinone (Fieser et al., J. Am. Chem. Soc., 1948, 70, 3151).

In spite of the fact that in literature the attempts of acylating the compound II were reported as fruitless or non interesting because of the low yields, the 5,8-dimethoxy-3, 4-dihydronaphthalene II is treated with acetyl chloride in the presence of an excess of aluminium trichloride, preferably 5–9 moles of aluminium trichloride for one mole of acyl chloride, at the temperature of −35°+25° C., preferably at 0° C. After the usual work-up and crystallisation with ethyl acetate, the product, 2-acetyl-5,8-dimethoxy-3,4-dihydronaphthalene is obtained in yields higher than 70%.

Compound III is stereoselectively converted to diol IV by a Sharpless asymmetric dihydroxylation which is described in literature for other olefin substrates (Sharpless et al., Chem. Rev. 1994, 94, 2483). The reactive used in this step is AD-mix α (catalogue Aldrich, reactive 39275-8, see also J. Org. Chem. 1992, 57, 2768) with a further addition of the osmium salt ($K_2OsO_2(OH)_4$) and methanesulphonamide.

The osmium salt is always in catalytic quantity vis-a-vis the substrate. The reaction is performed at low temperature, −4 e+20° C., preferably at 0° C., the yield is 70%, with an enantiomeric excess higher than 95%.

The optically. active diol IV is converted into a chloroacetate V through the formation "in situ" of a cycle intermediate using trimethylortoacetate in the presence of an acid catalyst followed by treatment with trimethylsilyl chloride according to a method already described in literature for different dioles (Sharpless et al. Tetrahedron, 1992, 48, 10515).

This step gives yields higher then 80%.

The reduction of the chloroacetate to acetate VI can be performed photochemical or by thermic treatment in the presence of tributyltinhydride and radical precursors as AIBN or BPO or by catalytic hydrogenation.

The yields are higher then 80%.

The acetate can be obtained directly by catalytic reduction of diol IV.

The hydrolysis of the acetate can be performed with ionic exchange resins in quantitative yield. Alternatively the known methods for the hydrolysis of the acetates, as the treatment with sodium methoxide or sodium hydroxide.

What reported in Scheme I can be easily applied to the synthesis of all the compounds of formula I, using the corresponding starting products.

The tetraline I which is an object of the present invention is therefore obtained in only 4–5 steps with a total yield much higher than the one reported for the known processes.

Moreover, the reaction conditions as described make it possible the industrial scale up of the process. The subsequent steps of the process through the anthracyclinone to the final anthracycline are performed as described in literature.

The process according to the invention will be better understood in the light of the hereinafter reported Example which refers to the Scheme 1 i.e. to the preparation of the tetraline of formula I wherein $R=CH_3$.

EXAMPLE 1

Synthesis of III

To a suspension of aluminium trichloride (449 g) in dichloromethane (2 l) in nitrogen current, acetyl chloride (380 ml) is added drop by drop at 0° C. After 30 min. stirring at 0° C., to the so obtained solution a solution of 5,8-dimthoxy-3,4-dihydronaphthalene II (80 g) in dichloromethane (2,5 l) is slowly added drop by drop. After 30 min stirring at 0° C. the mixture was hydrolysed with ice. After separation of the organic phase and washing with HCl 1N (3×6 l), $H_2O$ (3×4 l) and brine (2×4 l), the solvent was evaporated u.v. at 40° C. giving a yellow solid residue (98 g). By crystallisation from refluxing ethyl acetate 71 g of the desired compound III where obtained.

Yield 73%. $^1H$ NMR ($CDCl_3$): 2.44 (s, 3H, $H_{10}$); 2.53 (m, 2H, $H_6$); 2.80 (m, 2H, $H_5$); 3.30, 3.84 (2s, 6H, $OCH_3$); 6.75 (dd, 2H, $H_2+H_3$); 7.81 (m, 1H, $H_8$); $^{13}C$ NMR ($CDCl_3$): 19.9, 20.5 ($C_5$, $C_6$); 25.3 ($C_{10}$); 55.9, 56.1 ($OCH_3$); 108.5, 113.2 ($C_2$, $C_3$); 122.6, 127.2 ($C_{4a}$, $C_{8a}$); 131.5 ($C_8$); 137.2 ($C_7$); 150.4, 151.0 ($C_1$, $C_4$); 198.8 ($C_9$). TLC: r.f. 0.80 (Petrol ether/Ethyl acetate=80/20). HPLC: r.t.=8.9 min (Conditions: Lichrospher 100 RP 18 (5, μm, 250×4 mm) $CH_3CN/H_2O+$ 0.1% TFA=60/40; 1 ml/min; λ=214 nm; 20 μl of a solution 1 mg/10 ml)

EXAMPLE 2

Synthesis of IV

To a solution of AD mix-α (600 g) and $K_2OsO_2(OH)_4$ (1 g) in water (2 l) t-butanole (2.15 l), methansulphonammide (40.7 g), sodium bicarbonate (109 g) are added. The mixture was stirred up to complete solution of the solid components, cooled down at 0° C., added with 4-acetyl-3,4-dihydronaphthalene (100 g) and vigorously stirred for 96 h.

After complete reaction of the precursor, checked by TLC (Petrol ether/ethyl acetate=80/20), 630 g of sodium bisulphite are added in portions and, after 1 h stirring, 4 l of AcOEt are added and the phases are separated.

The organic phase was washed with NaOH 1N (1×2 l), $H_2O$ (1×2 l) and evaporated under vacuum.

The obtained solid was solved in 750 ml $CH_2Cl_2$ and the solution was extracted with $H_2SO_4$ 3% saturated with $K_2SO_4$ (4×200 ml), $NaHCO_3$ s.s. (1×300 ml) and $H_2O$ (1×300 ml).

The organic phase, dried on anhydrous $MgSO_4$, was evaporated under vacuum leaving a solid residue.

The product was crystallised from AcOEt/cyclohexane= 1/1, filtered and dried under vacuum.

78.7 g of a crystalline solid were obtained. Yield: 70.5% $^1H$ NMR ($CDCl_3$): 1.87 (m, 2H, $H_6$); 2.38 (s, 3H, $H_{10}$); 2.79 (m, 2H, $H_5$); 3.78, 3.84 (2s, 6H, $OCH_3$); 3.81 (m, 1H, $H_8$); 4.87 (d, 1H, $OH_8$); 5.29 (s, 1H, $OH_7$); 6.71 (s, 2H, $H_2+H_3$). $^{13}C$ NMR ($CDCl_3$): 19.1 ($C_{10}$); 25.8 ($C_5$); 28.7 ($C_6$); 55.7, 55.7 ($OCH_3$); 68.5 ($C_8$); 78.7 ($C_7$); 108.0, 108.8 ($C_2$, $C_3$); 125.8, 127.1 ($C_{4a}$, $C_{8a}$); 151.1, 152.3 ($C_1$, $C_4$); 214.2 ($C_9$). TLC: r.f. 0.25 (Petrol ether/Ethyl acetate=80/20) HPLC: r.t.=4.1 min (Conditions: Lichrospher 100 RP 18 (5 μm) 250×4 mm $CH_3CN/H_2O+0.1\%$ TFA=50/50; 1 ml/min; λ=214 nm; 20 μl of a solution 2.8 mg/10 ml) e.e.=98% determined by chiral HPLC (Conditions: Chiralcel OD 250×4.6 mm; n-hexane/EtOH=90/10; 1 ml/min; λ214 nm; 20 μl of a solution 1.3 mg/10 ml) m.p.=141–143° C. $[\alpha]_D^{25}=-21.9°$ (c=1.0, $CHCl_3$)

EXAMPLE 3

Synthesis of V

To a solution of diol (77 g) in $CH_2Cl_2$ (600 ml), under nitrogen, trimethylortoacetate (59.3 ml) and piridiniumtoluene-4-sulphonate (2 g) are added.

The solution is stirred at room temperature for 24 H. The solvent is evaporated under vacuum leaving a solid residue.

The solid was solubilised $CH_2Cl_2$ (600 ml) and added, under nitrogen, with trimethylsilyl chloride (65 ml). The reaction mixture is stirred at room temperature for 1 h and, after evaporation of the solvent under vacuum, was treated with cyclohexane (400 ml) under vigorous stirring for 3 h.

The solid was filtered and dried under vacuum.

98.1 g of the desired product were obtained (quantitative yield).

$^1H$ NMR ($CDCl_3$): 1.96 (s, 3H, $H_{10}$); 1.97–3.15 (m, 4H, $H_5+H_6$); 2.43 (s, 3H, $H_{12}$); 3.81, 3.87 (2s, 6H, $OCH_3$); 5.35 (d, 1H, $H_8$); 6.76 (dd, 2H, $H_2+H_3$); $^{13}C$ NMR ($CDCl_3$): 19.6 ($C_{11}$); 20.2, 20.5 ($C_5$, $C_6$); 26.3 ($C_{12}$); 52.9 ($C_8$); 55.6, 56.0 ($OCH_3$); 82.9 ($C_7$); 108.3, 110.1 ($C_2$, $C_3$); 123.2, 125.4 ($C_{4a}$, $C_{8a}$); 150.7, 151.6 ($C_1$, $C_4$); 169.6 ($C_{11}$); 204.2 ($C_9$). TLC: r.f.=0.55 (Petrol ether/AcOEt=75/25) m.p.=128–138° C. $[\alpha]_D^{25}=-16.2°$ (c=1.0, $CH_2Cl_2$).

EXAMPLE 4

Synthesis of VI

To a solution of chloacetate (97.3 g) in toluene (2 l) AIBN (1.5 g) and tributyl-tinhydrure (225 ml) were added in nitrogen current. The mixture was stirred under the light of a 200 Watt wolfram 1 amp for 24 h and thereafter extracted with water (500 ml). The organic phase is separated, dried and evaporated under vacuum. The residue is treated with cyclohexane (500 ml) under stirring, filtered and dried under vacuum at 40° C.

67.8 g of the desired product are obtained in the form of a white solid.

Yield: 80.3%. $^1$H NMR (CDCl$_3$): 1.95, 2.50 (2m, 2H, H$_6$); 2.05 (1.3H, H$_{10}$); 2.22 (1.3H, H$_{12}$); 2.40, 2.90 (2m, 2H, H$_5$); 3.00 (dd, 2H, H$_8$); 3.77, 3.80 (2s, 6H, OCH$_3$); 6.66 (m, 2H, H$_2$+H$_3$). $^{13}$C NMR (CDCl$_3$): 19.5, 21.0 (C$_5$, C$_6$); 24.0 (C$_{10}$); 26.7 (C$_{12}$); 30.2 (C$_8$); 55.6, 55.5 (OCH$_3$); 83.6 (C$_7$); 107.0, 107.2 (C$_2$, C$_3$); 122.7, 125.1 (C$_{4a}$, C$_{8a}$); 150.9, 151.4 (C$_1$, C$_4$); 170.5 (C$_{11}$); 206.5 (C$_9$). TLC: r.f.=0.28 (Toluene/Ethylacetate=95/5) HPLC: r.t.=7.4 min (Conditions: Lichrospher 100 RP 18 (5 μm) 250×4 mm, CH$_3$CN/H$_2$O+0.1% TFA=60/40; 1 ml/min; λ=214 nm; 20 μl of a solution 1.2 mg/10 ml) m.p.: 110–118° C. [α]$_D^{25}$: −46.3° (c=1.0, CHCl$_3$).

EXAMPLE 5

Synthesis of I

To a solution of acetate (66 g) in methanol (5 l) the Amberlite IRA-400 resin (OH) (183 ml) previously activated by treatment with NaOH 30% (8×400 ml) and washed with water (5×400 ml) and methanol (4×400 ml) was added. The reaction mixture is stirred for a night at room temperature. After removal of the resin by filtration and evaporation of the solvent under vacuum a solid residue was obtained which after crystallisation from cyclohexane/ethylacetate, filtration and drying gave 51.85 g of desired product.

Yield: 92%. $^1$H NMR (CDCl$_3$): 1.89 (m, 2H, H$_6$); 2.33 (s, 3H, H$_{10}$); 2.91 (m, 4H, H$_5$+H$_8$); 3.65 (s, 1H, OH); 3.77, 3.80 (2s, 6H, OCH$_3$); 6.66 (s, 2H, H$_2$+H$_3$). $^{13}$C NMR (CDCl$_3$): 19.2 (C$_5$); 23.9 (C$_{10}$); 29.7, 32.4 (C$_6$, C$_8$); 55.5, 55.6 (OCH$_3$); 76.4 (C$_7$); 107.0, 107.4 (C$_2$, C$_3$); 122.7, 125.5 (C$_{4a}$, C$_{8a}$); 151.1, 151.6 (C$_1$, C$_4$); 212.3 (C$_9$). TLC: r.f.=0.27 (Petrol ether/Ethylacetate=80/20 HPLC: r.t.=5.9 min (Conditions: Lichrospher 100 RP 18 (5 μm) 250×4 mm, CH$_3$CN/H$_2$O+0.1% TFA=50/50; 1 ml/min; λ=214 nm; 20 μl of a solution 2.5 mg/ml) e.e=>99% determined by chiral HPLC (Conditions: Chiralcel OD 250×4.6 mm; n-hexane/EtOH=90/10; 1 m/min; λ214 nm; 20 μl of a solution 1.35 mg/10 ml) m.p.: 126–129° C. [α]$_D^{25}$=−46.20 (c=1.0, CHCl$_3$)

SCHEME I

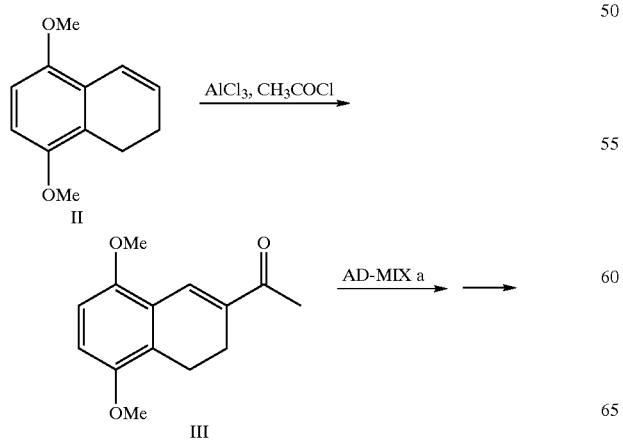

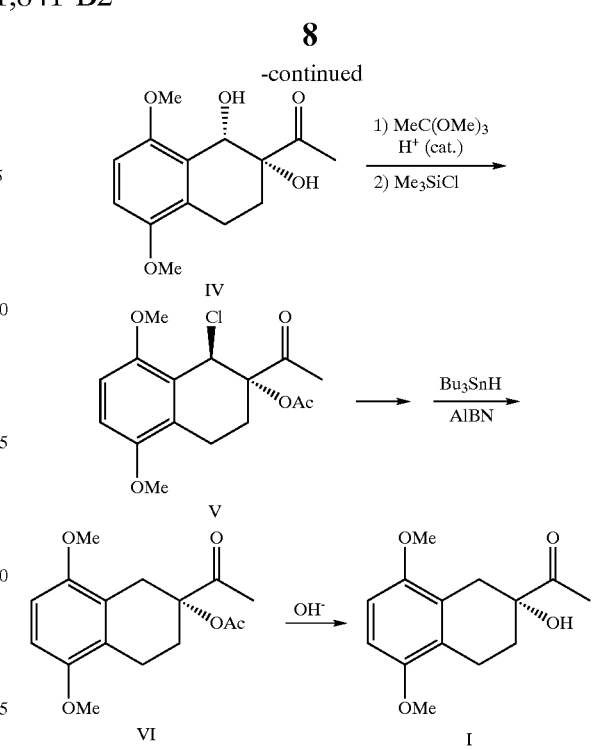

What is claimed is:
1. Optically active compound of formula V:

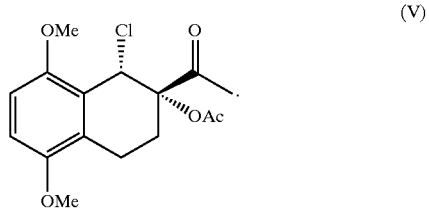

2. Process for the preparation of intermediate of formula (I):

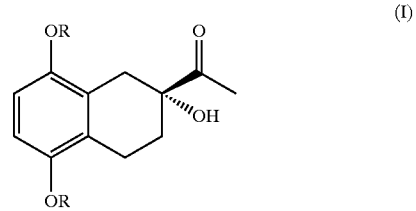

wherein: R=C$_{1-3}$ alkyl capable of being used in the preparation of anthracyclines of formula VIII:

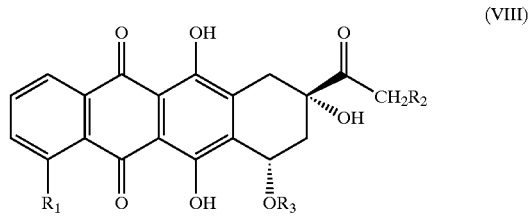

wherein R$_1$=H, OH, or OCH$_3$; R$_2$=H or OH; R$_3$=X, Y or Z where:

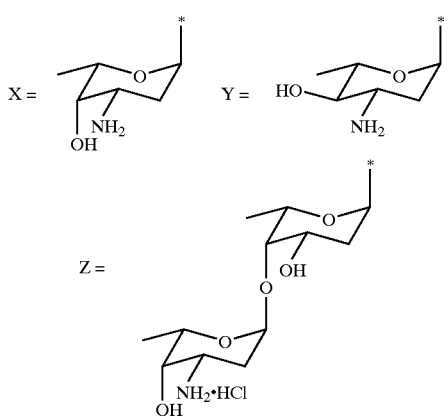

comprising the steps of:

starting from a 5-dialkoxy-3,4-dihydronaphthalene of formula (II):

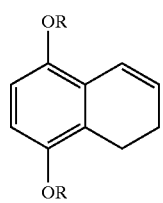

(II)

wherein R=C$_{1-3}$ alkyl formula (I) is prepared according to the following steps:

a) the 5,8-dialkoxy-3,4-dihydronaphthalene of formula (II), is acylated in a single step with acetyl chloride in the presence of an excess of AlCl$_3$ at a temperature comprised between −35° and 25° C., forming the corresponding acyl derivative (III):

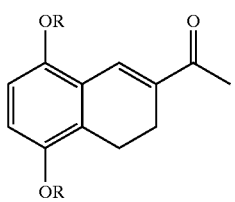

(III)

wherein R=C$_{1-3}$ alkyl;

b) the acyl derivative (III) is enantioselectively hydroxylated with a catalytic quantity of osmium, to form the diol (IV):

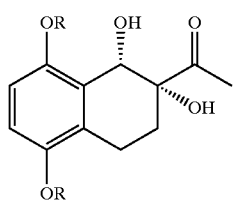

(IV)

wherein R=C$_{1-3}$ alkyl;

c) the diol (IV) is converted into the acetate (VI):

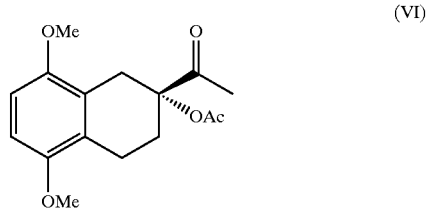

(VI)

by direct reduction or, alternatively, through the chloroacetate (V):

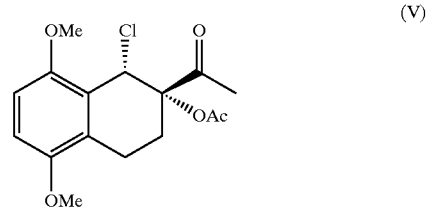

(V)

by reaction with triethylortoacetate and trimethylsilylchloride followed by reduction d)the acetate (VI) is hydrolyzed to the tetralin of formula (I).

3. Process according to claim 2 wherein the tetralin of formula (I) is used as an intermediary in the production of anthracyclinone of formula (VII):

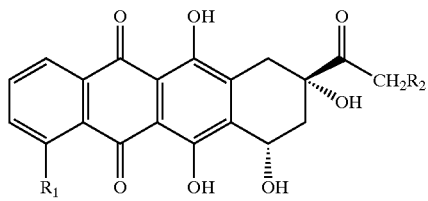

VII wherein R$_1$=H, OH, or OCH$_3$;
R$_2$=H, OH or O-acyl, wherein acyl is chosen between formyl, acetyl, mono- or di-chloroacetyl capable of being converted into the anthracycline of formula (VIII):

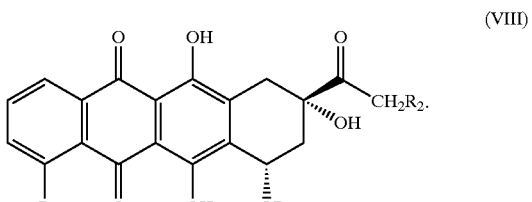

(VIII)

4. Process according to claim 2 wherein R=methyl and R$_2$=O-acetyl.

5. Process according to claim 2 wherein the acylation is performed at 0° C.

6. Process according to claim 2 wherein the enantioselective dihydroxylation according to step (b) is performed using catalytic quatities of osmium using the reactive AD-mix ∝ with a further addition of an osmium salt and methanesulphoneamide.

7. Process according to claim 6 wherein the osmium salt used is K$_2$OSO$_2$(OH)$_4$.

8. Process according to claim 7 wherein the reaction is performed at −4–+20° C.

9. Process according to claim 8 wherein the reaction is performed at 0° C.

10. Process according to claim 9 wherein the anthracyclines of formula (VIII) are: daunomicin (VIII, wherein $R_1$=OCH$_3$, $R_2$=H, $R_3$=X), doxorubicin (VIII wherein: $R_1$=OCH$_3$, $R_2$=OH, $R_3$=X), l'hydrarubicin (VIII wherein $R_1$=H, $R_2$=H, $R_3$=X) l'epirubicin (VIII, wherein: $R_1$=OCH$_3$, $R_2$=OH, $R_3$=Y), or a tetracycline of formula VIII wherein: $R_1$=H, $R_2$=OH, $R_3$=Z, where X, Y, and Z are defined as

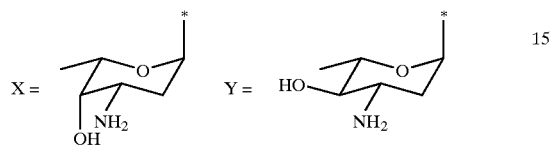

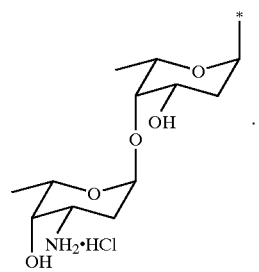

* * * * *